US006284911B1

(12) United States Patent
Allen et al.

(10) Patent No.: US 6,284,911 B1
(45) Date of Patent: Sep. 4, 2001

(54) SYNTHESIS OF VINYL CARBONATES FOR USE IN PRODUCING VINYL CARBAMATES

(75) Inventors: David Lewis Allen, Whiteville, NC (US); Heather Fort Henry, Covington, KY (US); Becky Lynn Cahill, Wilmington, NC (US); John Ponton, Jr., Wilmington, NC (US); Kathryn Marie Church, Wilmington, NC (US)

(73) Assignee: Wright Chemical Corporation, Reigelwood, NC (US)

( * ) Notice: Subject to any disclaimer, the term of this patent is extended or adjusted under 35 U.S.C. 154(b) by 0 days.

(21) Appl. No.: 09/606,032

(22) Filed: Jun. 28, 2000

Related U.S. Application Data

(60) Provisional application No. 60/141,547, filed on Jun. 29, 1999.

(51) Int. Cl.[7] .................................................. C07C 69/96
(52) U.S. Cl. .......................................... 558/270; 558/277
(58) Field of Search ..................................... 558/270, 277

(56) References Cited

U.S. PATENT DOCUMENTS

| | | | |
|---|---|---|---|
| 3,472,888 | 10/1969 | Bazouin et al. ................... | 260/448.8 |
| 3,696,150 | 10/1972 | Lichstein et al. .................. | 260/544 F |
| 4,294,975 | 10/1981 | Takago et al. ...................... | 556/482 |
| 4,377,706 | 3/1983 | Hallgren ............................... | 556/482 |
| 4,612,143 | 9/1986 | Piteau et al. ......................... | 558/282 |
| 4,622,408 | 11/1986 | Duggan ................................. | 548/533 |
| 4,697,032 | 9/1987 | Malfroot et al. ...................... | 558/270 |
| 4,783,543 | 11/1988 | Schulz, Jr. et al. ................... | 556/446 |
| 4,808,745 | 2/1989 | Malfroot et al. ..................... | 558/277 |
| 4,973,728 | 11/1990 | Tuinstra et al. ....................... | 558/268 |
| 5,070,215 | 12/1991 | Bambury et al. ..................... | 556/418 |
| 5,113,007 | 5/1992 | Combret et al. ..................... | 556/482 |
| 5,260,000 | 11/1993 | Nandu et al. ......................... | 264/2.1 |
| 5,352,816 | 10/1994 | Takeoka ............................... | 556/420 |
| 5,384,342 | 1/1995 | Szum ................................... | 522/172 |
| 5,428,176 | 6/1995 | Weigel ................................. | 549/214 |
| 5,532,398 | 7/1996 | Wolter et al. ........................ | 556/420 |
| 5,610,252 | 3/1997 | Bambury et al. .................... | 526/279 |

FOREIGN PATENT DOCUMENTS

| | | | |
|---|---|---|---|
| 2603886 | 3/1988 | (FR) | C07C/69/96 |

OTHER PUBLICATIONS

Emsley et al. "Kinetic and Euilibrium Studies by 19F Nuclear Magnetic Resonance of the Formation Acetyl Fluoride from Acetyl Chloride and Tetraethylammonium Fluoride in Acetic Acid, " *Journal of the Chemical Society; Perkin Translations2* 923–925 (1988).

Olofson et al. A Regiospecific and Stereospecific Route to Enol Carbonates and Carbamates: Closer Look at a "Naked Anion," *Tetrahedron Letters* 21:819–822 (1980).

Olofson et al. "Useful Route to Alkenyl S–Phenyl Thiocarbonates: Reagents for the Introduction of the Enyloxycabonyl Moiety in Synthesis," *Journal of Organic Chemistry* 45:2538–2541 (1980).

International Search Report; PCT/US00/17820; Date of Mailing: October 19, 2000.

*Primary Examiner*—Jane C. Osowecki
*Assistant Examiner*—Joseph Murray
(74) *Attorney, Agent, or Firm*—Myers Bigel Sibley & Sajovec, P.A.

(57) ABSTRACT

A method for making a vinyl carbonate represented by the formula (I):

$$CH_2=CHOC(O)X_1R_1 \quad (I)$$

wherein $X_1$ is oxygen or sulfur and $R_1$ is a substituted or an unsubstituted aliphatic alkyl, aryl, aryl alkyl, olefinic, vinyl, or cycloaliphatic group comprises:

(a) reacting a compound represented by the formula (II):

$$X_2C(O)X_1R_1 \quad (II)$$

wherein $X_2$ is a halogen other than fluorine, with a compound represented by the formula (III):

$$M_1\text{—}F \quad (III)$$

wherein $M_1$ is selected from a Group IA metal, in the presence of a first phase transfer catalyst and a first organic solvent, to form a compound represented by the formula (IV):

$$FC(O)X_1R_1 \quad (IV);$$

and (b) reacting a compound represented by the formula (IV) with a compound represented by the formula (V):

$$CH_2=CHOSi(R_2)_3 \quad (V)$$

wherein $R_2$ is a substituted or an unsubstituted aliphatic alkyl, aryl, aryl alkyl olefinic, vinyl, or cycloaliphatic group, or any combination thereof, in the presence of a metal salt represented by the formula $M_2$—F wherein $M_2$ is a Group IA metal, a second phase transfer catalyst, and a second organic solvent, to form the compound represented by formula (I).

24 Claims, No Drawings

SYNTHESIS OF VINYL CARBONATES FOR USE IN PRODUCING VINYL CARBAMATES

CROSS-REFERENCE TO RELATED APPLICATIONS

The instant application claims priority to U.S. Provisional Application Ser. No. 60/141,547 filed Jun. 29, 1999, the disclosure of which is incorporated herein by reference in its entirety.

FIELD AND BACKGROUND OF THE INVENTION

The invention generally relates to methods of forming vinyl carbonates, particularly those used in forming vinyl carbamates.

Vinyl chloroformate is a monomer used in various applications such as, for example, the making of contact lenses. Currently, it is believed that this compound is only available via a multi-step synthesis involving the use of phosgene and organomercury intermediates. These intermediates are undesirable in that they present heightened environmental concerns. Therefore, it would be desirable to provide a synthetic method which does not necessitate the use of phosgene and organomercury intermediates.

SUMMARY OF THE INVENTION

The present invention addresses the above shortcomings and provides methods for making vinyl carbonates and carbamates which do not necessitate the use of phosgene and organomercury intermediates.

In one aspect, the invention provides a method for making a vinyl carbonate represented by the formula (I):

$$CH_2=CHOC(O)X_1R_1 \qquad (I)$$

wherein $X_1$ is oxygen or sulfur and $R_1$ is a substituted or an unsubstituted aliphatic alkyl, aryl, aryl alkyl, olefinic, vinyl, or cycloaliphatic group.

Preferably, the compound represented by formula (I) is a vinylphenyl carbonate in which instance $R_1$ is a substituted or an unsubstituted aryl group. The method comprises:

(a) reacting a compound represented by formula (II):

$$X_2C(O)X_1R_1 \qquad (II)$$

wherein $X_2$ is a halogen other than fluorine, with a compound represented by formula (III):

$$M_1-F \qquad (III)$$

wherein $M_1$ is selected from a Group IA metal, in the presence of a first phase transfer catalyst and a first organic solvent, to form a compound represented by formula (IV):

$$FC(O)X_1R_1 \qquad (IV)$$

and;

(b) reacting a compound represented by formula (IV) with a compound represented by formula (V):

$$CH_2=CHOSi(R_2)_3 \qquad (V)$$

wherein $R_2$ is a substituted or an unsubstituted aliphatic alkyl, aryl, aryl alkyl olefinic, vinyl, or cycloaliphatic group, or any combination thereof, in the presence of a metal salt represented by the formula $M_2-F$ wherein $M_2$ is a Group IA metal, a second phase transfer catalyst, and a second organic solvent or solvent combination, to form the compound represented by formula (I).

In a preferred embodiment, the above method further comprises the step of reacting the compound represented by formula (I) with a compound represented by formula (VI):

$$NHR_3 R_4 \qquad (VI)$$

wherein $R_3$ and $R_4$ may be the same or different and are selected from a substituted or unsubstituted aliphatic alkyl, aryl, aryl alkyl, olefinic, cycloaliphatic, hydrogen or combinations thereof, to form a compound represented by formula (VII):

$$R_3R_4NC(O)OCH=CH_2 \qquad (VII).$$

In another preferred embodiment, the above method further comprises the step of reacting a compound represented by the formula (I) with a compound represented by the formula (VIII):

$$HO-R_5 \qquad (VIII)$$

wherein $R_5$ is selected from an unsubstituted or substituted aliphatic alkyl, aryl, aryl alkyl, olefinic, or cycloaliphatic group, to form a compound represented by the formula (IX):

$$R_5-O-C(O)OCH=CH_2 \qquad (IX)$$

In another embodiment, the invention provides a method of forming a carbonate of the formula:

$$R'-O-C(O)-O-R' \qquad (XVI)$$

wherein R' is substituted or unsubstituted alkyl, aryl, aryl alkyl, vinyl, olefinic, or cycloaliphatic group. The method comprises:

reacting a carbonate of the formula (XVII):

$$R'-O-C(O)-O-R'' \qquad (XVII)$$

wherein R' and R" are different and are selected from substituted or unsubstituted alkyl, aryl, aryl alkyl, vinyl, olefinic, cycloaliphatic or any non-equivalent combination thereof (i.e., R' does not equal R"), in the presence of: (1) a metal fluoride and a phase transfer catalyst or (2) a quaternary ammonium fluoride species to form the compound of formula (XVI) and a compound of the formula R"—O—C(O)OR".

DETAILED DESCRIPTION OF THE PREFERRED EMBODIMENT

The invention will now be described with respect to embodiments described herein. It should be appreciated however that these embodiments are for the purposes of illustrating the invention, and are not to be construed as limiting the scope of the invention as defined by the claims.

The foregoing described substituents that can be used in the methods of the invention.

Preferred embodiments of $R_1$ include, without limitation, Ø-, p-NO$_2$Ø-, p-ClØ-, and $CH_2=CH-$. Functional groups and isomers thereof of these embodiments can also be employed.

$X_1$ may be oxygen or sulfur.

$X_2$ is a halogen, preferably one of the halogens chlorine, bromine, or iodine (i.e., other than fluorine).

$M_1$ and $M_2$ are independently selected from one of the Group IA metals, such as, for example, lithium, sodium, potassium, and the like.

$R_2$ may be selected from unsubstituted or substituted aliphatic alkyl, aryl, aryl alkyl, olefinic, vinyl, cycloaliphatic, or any combination thereof.

$R_5$ may be selected from unsubstituted or substituted aliphatic alkyl, aryl, aryl alkyl, olefinic, or cycloaliphatic.

$R_2$ is preferably $(CH_2)_q CH_3$ wherein q ranges from 0 to 6, and is most preferably $CH_3$ or an aryl group which is most preferably phenyl.

$R_5$ is preferably $CH_2=C((CH_2)_p CH_3)CO_2(CH_2)_s$ wherein p ranges from 0 to 6 and is most preferably 0 and s ranges from 1 to 6, and is most preferably 2.

$R_3$ and $R_4$ may be independently selected from unsubstituted or substituted aliphatic alkyl, aryl, aryl alkyl, olefinic, cycloaliphatic, or hydrogen, or any combination thereof. In one preferred embodiment, $R_3$ is hydrogen and $R_4$ is a group represented by the formula:

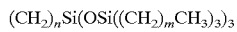

$(CH_2)_n Si(OSi((CH_2)_m CH_3)_3)_3$ wherein n ranges from 0 to 6 (preferably is 3) and m ranges from 0 to 6 (preferably is 0).

The first and second phase transfer catalysts may be independently selected from those that are known to one skilled in the art, particularly those employed in disproportionation reactions. For the purposes of the invention, the term "phase transfer catalyst" is construed to mean any chemical that can assist in the transfer of a reactive species from one phase (e.g., a solid or liquid phase) to another phase in order to facilitate a chemical reaction in this phase.

Exemplary phase transfer catalysts include, without limitation, crown ethers (e.g., 15-crown-5 or 1,4,7,10,13-pentaoxacyclopentadecane, 18-crown-6 or 1,4,7,10,13,16-hexaoxacyclooctadecane, organoammonium salts, and phosphonium salts.

Various organic solvents, such as those employed for the first and second organic solvents (which can be independently selected) can include those which are known to those skilled in the art. Exemplary organic solvents include, for example, polar, aprotic solvents such as, without limitation, dimethyl formamide ("DMF"), acetonitrile, dimethyl sulfoxide ("DMSO"), and the like. Non-polar organic solvents can also be used such as, without limitation, hexane(s), heptane, toluene, cyclohexane, and the like, along with ether-like solvents such as, but not limited to, diethyl ether, tetrahydrofuran ("THF"), methyl-t-butyl ether (MTBE), the glymes, and the like. Combinations of any of these solvents may be used.

Bases which can be used in the synthesis scheme may include those which are known to one skilled in the art. For example, organic bases may be employed such as, without limitation, 1,8-diazabicyclo[5.4.0.]undec-7-ene (DBU), triethylamine, N-methylimidazole and the like. Combinations of the above can also be used.

An example of a synthetic scheme for producing vinyl carbonates and vinyl carbamates in accordance with the invention is as follows:

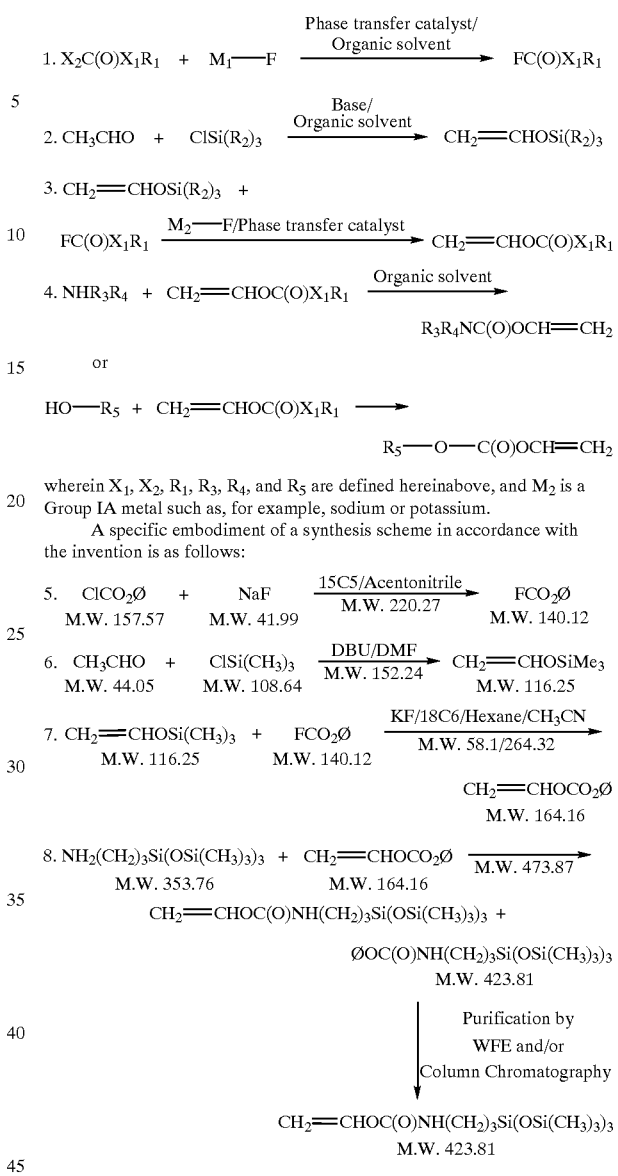

wherein $X_1$, $X_2$, $R_1$, $R_3$, $R_4$, and $R_5$ are defined hereinabove, and $M_2$ is a Group IA metal such as, for example, sodium or potassium.

A specific embodiment of a synthesis scheme in accordance with the invention is as follows:

Various techniques may be employed for purifying the carbonate and/or carbamate products formed by methods of the invention. Examples of purification techniques include, but are not limited to, wiped film evaporation (WFE), column chromatography (including flash and other pressure types as well as simulated moving bed techniques), selective reactivity, low temperature crystallization and/or trituration, and zone refining. These techniques may be used alone or in combination.

In various embodiments, the compound of formula (VII) may be present in a mixture along with a compound of the formula (XVIII):

$$ØX_1C(O)NR_3R_4 \qquad \qquad (XVIII)$$

wherein $R_3$ and $R_4$ may be the same or different substituted or unsubstituted alkyl, aryl, aryl alkyl, cycloaliphatic or olefinic group, or a combination thereof, and wherein the aromatic substituent may be substituted or unsubstituted. The compound of formula (XVIII) is often a by-product of the reaction which forms the compound of formula (VII). In such embodiments, the method of the invention may optionally further comprise the step of reacting the compound of formula (XVIII) with a compound of formula (XIX):

wherein $R_6$ and $R_7$ are individually selected from hydrogen, a substituted or unsubstituted alkyl, aryl, aryl alkyl, cycloaliphatic or olefinic group, or any combination thereof The amine selectively reacts with the compound of formula (XVIII) relative to the compound of formula (VII). In one embodiment, the aromatic substituent may be a substituted or unsubstituted aromatic or heteroaromatic, or their corresponding polycyclic analogs, such as, without limitation, phenyl, biphenyl, napthyl, or a polymer bound analog. The amine purification is advantageous in that it may be carried out directly in the same reaction vessel (e.g., pot) that produces the compounds of formulas (XVIII) and (VII) without any intermediate purification or washing steps.

Although not intending to be bound by theory, it is believed that the synthesis path for the selective reaction of the compound of formula (XVIII) may be as follows:

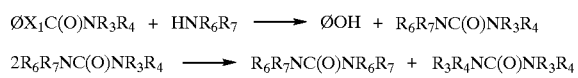

wherein $R_3$, $R_4$, $R_6$ and $R_7$ are defined above.

The above scheme is believed to be advantageous in that selective generation of mixed and symmetrical ureas are more easily separated from the vinyl carbamate of formula (VII) than is the aromatic carbamate of formula (XVIII).

The amine referred to above may be selected from various compounds known to one skilled in the art. Examples of amines include, without limitation, alkyl, heterocyclic, or aromatic amines. Examples of alkyl amines include primary and secondary amines. Specific examples include, without limitation, diethyl amine and ethylene diamine. Other bis-alkyl or aromatic amines can be used. The amine may be preferably used in an amount ranging from about 10 to about 50 mole percent based on the compound of formula (VI).

A number of processing conditions may be employed for selectively reacting the compound of formula (XVIII). In a preferred embodiment, the temperature employed during this method ranges from about 40° C. to about 80° C. under atmospheric pressure. The reaction time preferably is a minimum of 12 hours, and more preferably ranges from about 24 hours to about 72 hours. Preferably, the reaction proceeds until the compound of formula (XVIII) is substantially or completely reacted. The reaction mixture is thereafter preferably stripped under vacuum and the residue dissolved in a suitable organic solvent (e.g., hexane). Preferably, the solution is given aqueous washes, dried using appropriate materials (e.g., magnesium sulfate), then stripped to an oil under vacuum. The resulting product may then be purified in an appropriate manner if so desired.

In another aspect, the invention provides a method of forming a carbonate of the formula:

wherein R' is substituted or unsubstituted alkyl, aryl, aryl alkyl, vinyl, olefinic, or cycloaliphatic group. The method comprises reacting a carbonate of the formula (XVII):

wherein R' and R" are different and are selected from substituted or unsubstituted alkyl, aryl, aryl alkyl, vinyl, olefinic, cycloaliphatic or any combination thereof, in the presence of: (1) a metal fluoride and a phase transfer catalyst, or (2) a quaternary ammonium fluoride species to form the compound of formula (XVI). Although not intending to be bound by theory, the above reaction is believed to be a disproportionation reaction.

In one embodiment, the formula (XVI) is represented by the formula (X):

wherein $R_1$, $R_2$, and $R_3$ are independently selected from hydrogen, substituted or unsubstituted alkyl, aryl, aryl alkyl, vinyl, olefinic, cycloaliphatic or any combination thereof, and the formula (XVII) is represented by the formula (XI):

wherein $R_1$, $R_2$, and $R_3$ are defined above, and $R_4$ is selected from substituted or unsubstituted alkyl, aryl, aryl alkyl, vinyl, olefinic, or cycloaliphatic. Preferably, each of $R_1$, $R_2$, and $R_3$ are hydrogen, and $R_4$ is Ø.

Various metal fluorides may be employed in accordance with the invention such as, without limitation, fluorides of Group IA metals such as sodium, potassium, and lithium.

Any of the phase transfer catalysts described hereinabove can be used in the above reaction. Preferably, the phase transfer catalyst is a crown ether, with an exemplary crown ether being 18-crown-6.

Another aspect of the invention provides a method for the formation of a compound of formula (IX) by reacting a compound of formula (VIII) with a compound of formula (XVI) or (XVII). For example, the compound of formula (XVI) or the compound of formula (XVII) can be reacted with the compound of formula (XIV):

wherein n ranges from 1 to 10 and m ranges from 1 to 10 to form a compound of formula (XV):

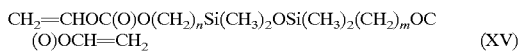

Preferably in this method, the compounds of formula (XVII) and (XVI) are represented by formula (XI) wherein each of $R_1$, $R_2$, and $R_3$ are hydrogen, and $R_4$ is Ø or vinyl.

An embodiment illustrating a general procedure for carrying out the methods of the invention is as follows. Modifications to this procedure may be made without departing from the spirit and scope of the invention. First, a reactant (e.g., chloroformate) is reacted in a polar solvent (e.g., acetonitrile) in a suitable reaction vessel at a specified temperature range (e.g., from about 20° C. to about 60° C.) with a metal fluoride (e.g., sodium fluoride) for a specified time period (e.g., about 10 to about 30 hours) in the presence of a phase-transfer agent (e.g., a crown ether such as 15-crown-5 for example). In a specific embodiment, the sodium chloride is filtered out, and the fluoroformate is isolated and purified by an acceptable technique (e.g., distillation).

Secondly, a second reactant (e.g., chlorotrialkylsilane) is reacted in a polar solvent (e.g., DMF) in the presence of a high-boiling base (e.g., DBU) with an aldehyde at a specified temperature (e.g., from about 20° C. to about 40° C.) for a specified time period (e.g., from about 4 to about 8 hours) to produce a product (e.g., a silyl enol ether). The product is isolated by a suitable technique (e.g., partial vacuum distillation), and purified by a suitable technique under appropriate pressure conditions (e.g., fractional distillation at atmospheric pressure).

Thirdly, the above-prepared intermediates are combined in a reaction performed in a solvent mixture composed of a polar and a non-polar solvent in a particular ratio under suitable processing conditions (e.g., at about 20° C. to about 60° C.) for a specified time period (e.g., about four to about eight hours) in the presence of catalytic amounts of a metal fluoride (e.g., potassium fluoride) and a phase-transfer catalyst (e.g., a crown ether such as 18-crown-6 for example). The metal fluoride is removed by a suitable procedure (e.g., silica gel treatment), and the product is thereafter isolated and purified by a suitable technique (e.g., distillation).

Fourth, the above-prepared vinyl carbonate may be reacted with an appropriate component (e.g., an alcohol or an amine) to yield the corresponding vinyl carbonate or vinyl carbamate. Such a reaction is preferably carried out in an ethereal solvent such as, for example, THF under specified processing conditions (e.g., from about 30° C. to about 50° C. for 6 to 24 hours). A non-polar solvent such as, for example, hexane may be used to advantage during washes of the reaction product for workup.

Further, in the case of carbamates derived from primary amines, contaminating side-product carbamates may be selectively removed by reaction with another amine as alluded to herein. This reaction is conducted under specified conditions (e.g., from about 40° C. to about 80° C. for about 24 to about 72 hours) sufficient to convert the non-vinyl carbamate to a symmetrical urea. The urea is typically more easily separated from the vinyl carbamate by common purification methods such as column chromatography than was the original non-vinyl carbamate. The side-product of this reaction is preferably phenol, from the preferred vinyl phenyl carbamate, which is easily removed from the workup via an appropriate technique (e.g., caustic wash).

Finally, symmetrical carbonates may be derived from unsymmetrical precursors by a disproportionation reaction. This reaction is effected by heating the original carbonate in the presence of catalytic amounts of a metal fluoride such as, e.g., potassium fluoride and a phase-transfer catalyst such as, e.g., a crown ether, 18crown-6 being an example. The lower-boiling symmetrical carbonate is removed from the reaction mixture via an appropriate technique (e.g., fractional distillation) as it is formed, then purified by known techniques, e.g., re-distillation.

Processing aids and/or additives known to one skilled in the art can be used in any of the above reactions if so desired. It should be appreciated that in certain instances the above solvents used in the above reactions may contain water or may be essentially or substantially free of water.

The invention will now be described in reference to the foregoing examples. It should be appreciated that these examples are for the purposes of illustrating the invention, and do not limit the scope of the invention as defined by the claims.

EXAMPLE 1

Synthesis of Phenylfluoroformate

To a solution of phenylchloroformate in acetonitrile is charged sodium fluoride. To this mixture is charged the 15-crown-5 ("15C5") at ambient temperature. The reaction mixture is then heated to 40° C. for approximately 16 hrs. Reaction completion is monitored by gas chromatography ("G.C.").

After cooling to room temperature, the mixture is filtered under nitrogen to remove the salt by-product. The solvent is removed via atmospheric distillation. The phenylfluoroformate product is then distilled at atmospheric pressure to give an approximate 85 percent theoretical yield of product (boiling point 150° C.–152° C.).

EXAMPLE 2

Synthesis of Vinyloxytrimethylsilane (VOTMS)

To a solution of DBU in DMF is slowly added chlorotrimethylsilane at a temperature below 30° C. over approximately 2 to 3 hrs. To this mixture is then added a solution of acetaldehyde in DMF over approximately 1 to 2 hours. The temperature of the reaction is maintained below 30° C. during the addition. The reaction mixture is stirred for 1 to 2 hours and checked for reaction completion by G.C. The volatile components are removed from the mixture via distillation under vacuum into a dry ice chilled receiver. The distillate from this flash distillation is then fractionally distilled at atmospheric pressure to give pure product in an approximate 70 percent theoretical yield. (boiling point: approximately 78° C.)

EXAMPLE 3

Synthesis of Vinylphenylcarbonate (VPC)

To a solution of phenylfluoroformate in hexanes and acetonitrile is charged potassium fluoride and 18-crown-6. The mixture is heated into solution at 40° C. Subsequently, vinyloxytrimethylsilane is slowly added at between 40° C. and 50° C. The mixture is further stirred for a minimum of two hours. Reaction progress is monitored by G.C. The solution is filtered through a short column of silica gel to remove potassium fluoride. The solvent is removed under reduced pressure and the product is vacuum distilled at 48° C. to 50° C. at 0.6 mm Hg at 80° C. to 82° C. at 6 mm Hg. The yield is determined to be approximately 70 percent of theoretical.

EXAMPLE 4

Synthesis of 3-[Tris(trimethylsiloxy)silyl]propyl Vinyl Carbamate

A solution of 3-aminopropyltris(trimethylsiloxy)-silane in THF is heated to 50° C. To this mixture is added a solution of vinylphenylcarbonate in THF with a mild exotherm being observed. Reaction completion is monitored by G.C. The reaction time is a minimum of one hour. The reaction is diluted with hexanes, washed with 2N HCl, saturated aqueous NaCl and dried over magnesium sulfate. The solvent is removed under reduced pressure and the crude product is purified by any one of the methods set forth herein, such as the method proposed in Example 6. Alternatively, this procedure can be combined with the purification technique as set forth in Example 5.

EXAMPLE 5

Synthesis of 3-[Tris(trimethylsiloxy)silyl]propyl Vinyl Carbamate

To a solution of 3-aminopropyltris(trimethylsiloxy)-silane in THF is added vinylphenylcarbonate, with a mild exotherm being observed. The solution is heated to 30° for a minimum of 6 hours. Reaction progress is monitored by G.C. Hexamethylene diamine is added to the reaction mixture, and the temperature raised to 60° for a minimum of 48 hours. Reaction progress is again monitored by G.C. The solvent is removed under reduced pressure, and the residue taken back up in hexanes. The solution is washed with 2N NaOH, 2N HCl, then saturated NaHCO₃ solution, and dried with magnesium sulfate. The solvent is removed under reduced pressure and the crude product is purified.

EXAMPLE 6

Treatment of Crude 3-[tris(trimethylsiloxy)silyl] propyl Vinyl Carbamate Reaction Mixture with Amines to Remove 3-[tris(trimethylsiloxy)silyl] propyl Phenyl Carbamate To a reaction mixture comprising crude 3-[tris(trimethylsiloxy)silyl]propyl vinyl carbamate containing the contaminant 3-[tris(trimethylsiloxy)silyl]propyl phenyl carbamate is added an amine, including one chosen from but not limited to isopropyl or other primary alkyl or aromatic amine, diethyl amine or other secondary alkyl or aryl or heterocyclic amine, ethylene diamine or other bis-alkyl or aromatic amine and is preferably hexamethylene diamine. The reaction mixture is heated in the range from 40° C. to 65° C. for a minimum of twelve hours. The reaction progress is followed by G.C. until the contaminant is completely reacted. The reaction mixture is stripped under vacuum and the residue dissolved in hexane. The solution is given aqueous washes, dried with magnesium sulfate, then stripped to an oil under vacuum. The crude product is then purified.

EXAMPLE 7

Synthesis of 3-Carboxypropyl Vinyl Carbamate

A solution of -alanine, sodium hydroxide, THF and water is prepared at room temperature. To this mixture is added p-nitrophenyl vinyl carbonate, and the mixture is stirred at room temperature. Reaction completion is monitored by HPLC. The reaction time is a minimum of one hour. The reaction mixture is diluted with ethyl acetate, washed with 2N HCl, saturated aqueous NaCl, and dried over magnesium sulfate. The solvent is removed under reduced pressure and the crude product is purified.

EXAMPLE 8

Synthesis of Divinyl Carbonate

Vinylphenyl carbonate, potassium fluoride and 18-Crown-6 are charged to a flask equipped for vacuum distillation. The mixture is heated and the product distilled away from the residual diphenyl carbonate. The crude material is then redistilled under partial vacuum.

EXAMPLE 9

Synthesis of 1,3-Bis-[4-vinyloxycarbonyloxy)but-1-yl]tetramethyldisiloxane

A solution of bis-(4-hydroxybutyl)tetramethyldisiloxane, divinyl carbonate and xylene are heated for a minimum of 12 hours. Reaction completion is monitored by GC. The solvent is removed under reduced pressure and the crude product is purified.

EXAMPLE 10

Synthesis of 2-Methacryloxy-1-Ethyl Vinyl Carbonate

A solution of p-nitrophenyl vinyl carbonate, hydroxyethylmethacrylate, DMSO and sodium hydroxide is stirred at room temperature for a minimum of 12 hours. Reaction completion is monitored by G.C. The solution is drowned into water and the mixture extracted with ethyl acetate. The product solution is washed with water, dried with magnesium sulfate, then stripped to an oil under vacuum. The crude product is then purified.

The invention has been described with respect to the preferred embodiments set forth above. It should be appreciated however that these embodiments are for the purposes of illustrating the invention, and are not intended to limit the scope of the invention as defined by the claims.

That which is claimed:

1. A method for making a vinyl carbonate represented by the formula (I):

wherein $X_1$ is oxygen or sulfur and $R_1$ is a substituted or an unsubstituted aliphatic alkyl, aryl, aryl alkyl, olefinic, vinyl, or cycloaliphatic group, said method comprising:
(a) reacting a compound represented by the formula (II):

wherein $X_2$ is a halogen other than fluorine, with a compound represented by the formula (III):

wherein $M_1$ is selected from a Group IA metal, in the presence of a first phase transfer catalyst and a first organic solvent, to form a compound represented by the formula (IV):

and
(b) reacting a compound represented by the formula (IV) with a compound represented by the formula (V):

wherein $R_2$ is a substituted or an unsubstituted aliphatic alkyl, aryl, aryl alkyl olefinic, vinyl, or cycloaliphatic group, or any combination thereof, in the presence of a metal salt represented by the formula $M_2$—F wherein $M_2$ is a Group IA metal, a second phase transfer catalyst, and a second organic solvent, to form the compound represented by formula (I).

2. The method according to claim 1, wherein $R_1$ is selected from the group consisting of Ø-, p-NO₂Ø-, p-ClØ-, and CH₂=CH—.

3. The method according to claim 1, wherein the compound represented by formula (II) is ClCO₂Ø-.

4. The method according to claim 1, wherein the first and second phase transfer catalysts may be the same or different and are selected from the group consisting of a crown ether, an organoammonium salt, a phosphonium salt, and mixtures thereof.

5. The method according to claim 1, wherein the first phase transfer catalyst is 15crown-5 and the second phase transfer catalyst is 18-crown-6.

6. The method according to claim 1, wherein the first and second organic solvents may be the same or different and may be selected from the group consisting of a polar aprotic solvent, a non-polar organic solvent, and mixtures thereof.

7. The method according to claim 6, wherein the polar aprotic solvent is selected from the group consisting of dimethyl formamide, acetonitrile, dimethyl sulfoxide, and mixtures thereof.

8. The method according to claim 6, wherein the non-polar organic solvent is selected from the group consisting of hexane, heptane, toluene, cyclohexane, diethyl ether, tetrahydrofuran (THF), methyl t-butyl ether (MTBE), glycol ethers, and mixtures thereof.

9. The method according to claim 1, wherein $X_2$ is chlorine.

10. The method according to claim 1, wherein $M_1$ is sodium.

11. The method according to claim 1, wherein $M_2$ is potassium.

12. The method according to claim 1, wherein $R_2$ is $((CH_2)_qCH_3)$ wherein q ranges from 0 to 6.

13. A method for making a vinylphenyl carbonate represented by the formula (I):

$$CH_2=CHOC(O)X_1R_1 \qquad (I)$$

wherein $X_1$ is oxygen or sulfur and $R_1$ is a substituted or an unsubstituted aryl, said method comprising:
(a) reacting a compound represented by the formula (II):

$$X_2C(O)X_1R_1 \qquad (II)$$

wherein $X_2$ is a halogen other than fluorine, with a compound represented by the formula (III):

$$M_1\text{---}F \qquad (III)$$

wherein $M_1$ is selected from a Group IA metal, in the presence of a first phase transfer catalyst and a first organic solvent, to form a compound represented by the formula (IV):

$$FC(O)X_1R_1 \qquad (IV);$$

and
(b) reacting a compound represented by the formula (IV) with a compound represented by the formula (V):

$$CH_2=CHOSi(R_2)_3 \qquad (V)$$

wherein $R_2$ is a substituted or an unsubstituted aliphatic alkyl, aryl, aryl alkyl olefinic, vinyl, or cycloaliphatic group, or any combination thereof, in the presence of a metal salt represented by the formula $M_2$---F wherein $M_2$ is a Group IA metal, a second phase transfer catalyst, and a second organic solvent, to form the compound represented by formula (I).

14. The method according to claim 13, wherein $R_1$ is selected from the group consisting of Ø-, p-NO$_2$Ø-, p-ClØ-, and $CH_2=CH$---.

15. The method according to claim 13, wherein the compound represented by formula (II) is ClCO$_2$Ø-.

16. The method according to claim 13, wherein the first and second phase transfer catalysts may be the same or different and are selected from the group consisting of a crown ether, an organoammonium salt, a phosphonium salt, and mixtures thereof.

17. The method according to claim 13, wherein the first phase transfer catalyst is 15-crown-5 and the second phase transfer catalyst is 18-crown-6.

18. The method according to claim 13, wherein the first and second organic solvents may be the same or different and may be selected from the group consisting of a polar aprotic solvent, a non-polar organic solvent, and mixtures thereof.

19. The method according to claim 18, wherein the polar aprotic solvent is selected from the group consisting of dimethyl formamide, acetonitrile, dimethyl sulfoxide, and mixtures thereof.

20. The method according to claim 18, wherein the non-polar organic solvent is selected from the group consisting of hexane, heptane, toluene, cyclohexane, diethyl ether, tetrahydrofuran (THF), methyl t-butyl ether (MTBE), glycol ethers, and mixtures thereof.

21. The method according to claim 13, wherein $X_2$ is chlorine.

22. The method according to claim 13, wherein $M_1$ is sodium.

23. The method according to claim 13, wherein $M_2$ is potassium.

24. The method according to claim 13, wherein $R_2$ is $((CH_2)_qCH_3)$ wherein q ranges from 0 to 6.

* * * * *

UNITED STATES PATENT AND TRADEMARK OFFICE
CERTIFICATE OF CORRECTION

PATENT NO. : 6,284,911 B1
DATED : September 4, 2001
INVENTOR(S) : David Lewis Allen; Heather Fort Henry; Becky Lynn Cahill; John Ponton, Jr.; Kathryn Marie Church It is certified that error appears in the above-identified patent and that said Letters Patent is hereby corrected as shown below:

Title page,
OTHER PUBLICATIONS,
First entry, (Emsley et al.), after "Kinetic and" please correct spelling of "Equilibrium"
First entry, (Emsley et al.), after "*Perkin*" please insert a space between "*Translations*" and "2"
Second entry, (Olofson et al.) please insert a beginning quotation mark before "A Regiospecific ...

Signed and Sealed this

Twelfth Day of March, 2002

Attest:

Attesting Officer

JAMES E. ROGAN
*Director of the United States Patent and Trademark Office*